United States Patent [19]

Müller et al.

[11] 4,421,691
[45] Dec. 20, 1983

[54] PREPARATION OF FATTY ACID ESTERS

[75] Inventors: Wolfgang H. E. Müller; Peter Hofmann, both of Marl, Fed. Rep. of Germany

[73] Assignee: Chemische Werke Hüls AG, Marl, Fed. Rep. of Germany

[21] Appl. No.: 270,851

[22] Filed: Jun. 5, 1981

[30] Foreign Application Priority Data

Jun. 25, 1980 [DE] Fed. Rep. of Germany ....... 3023765

[51] Int. Cl.³ .................... C07C 67/04; C07C 67/38
[52] U.S. Cl. .............................. 260/410.9 R; 560/233
[58] Field of Search .................. 260/410.9 R, 410.9 C; 252/416, 431 N; 560/233

[56] References Cited

U.S. PATENT DOCUMENTS 3,507,891 4/1970 Hearne .............................. 260/410.9
3,856,832 12/1974 Keblys .............................. 260/410.9
4,041,057 4/1977 Fanning ............................ 260/410.9

FOREIGN PATENT DOCUMENTS 8024 11/1981 European Pat. Off. .
2912489 10/1980 Fed. Rep. of Germany .. 260/410.9 R

*Primary Examiner*—Thomas A. Waltz
*Attorney, Agent, or Firm*—Wells & Wells

[57] ABSTRACT

A process for preparing fatty acid esters by reacting olefins, aklanols and carbon monoxide in the presence of a compound of cobalt and a promoter consisting of pyridine, non-orthosubstituted alkylpyridines or mixtures thereof. The reaction output is at first treated with a gas containing oxygen in a non-damaging manner and then reprocessed in two distillation stages. The first distillation stage is operated at a higher pressure than the second. In the first distillation stage there is produced a distillate free of cobalt and a sump product containing all of the cobalt used as catalyst. In the second distillation stage the sump product of the first distillation stage is again distilled to produce another distillate free of cobalt and a cobalt concentrate as sump product. This cobalt concentrate is incorporated into pyridine, a non-orthosubstituted alkylpyridine or a mixture thereof to form a suspension. The suspension is then treated by a mixture of carbon monoxide and hydrogen at a temperature of 100° to 250° C. and a pressure at least 50 bars, and this treatment product is fed back into the fatty acid ester synthesis.

8 Claims, No Drawings

PREPARATION OF FATTY ACID ESTERS

CROSS REFERENCE TO RELATED APPLICATIONS

Applicants claim priority under 35 USC 119 for application P No. 30 23 765.1, filed June 25, 1980 in the Patent Office of the Federal Republic of Germany.

The disclosure of applicant Hofmann's copending application Ser. No. 125,482 filed Feb. 28, 1980 is incorporated herein as an example of an alkoxycarbonylation which uses olefins having internal double bonds as a starting material.

BACKGROUND OF THE INVENTION

The field of the invention is synthetically produced higher fatty esters and the present invention is particularly concerned with the production of fatty acid esters by reacting olefins, alkanols and carbon monoxide in the presence of a cobalt catalyst and a promoter.

It is known that fatty acids can be prepared by reacting olefins with carbon monoxide and compounds containing a replaceable hydrogen atom such as alkanols in the presence of a catalyst containing a metal of Group VIII of the Periodic Table of Elements and possibly also containing a promoter (J. Falbe, "Synthesen mit Kohlenmonoxid," Springer publishers, Berlin, Heidelberg, New York, 1967).

In a preferred variation of this invention, which is called alkoxycarbonylation, the conversion takes place in the presence of catalysts containing cobalt. The additional use of pyridine or of a non-orthosubstituted alkylpyridine as the promoter is found to be an especially preferred embodiment.

The state of the art of alkoxycarbonylation may be ascertained by reference to U.S. Pat. Nos. 3,507,891; 3,856,832 and 4,041,057, the disclosures of which are incorporated herein.

A significant problem relating to the homogeneously catalyzed alkoxycarbonylation reaction is an industrially simple and loss-free process of recovery of the relatively expensive cobalt from the reaction mixture in a form which permits its reuse as a catalyst.

In the processes described in West German published application No. 19 63 804 and U.S. Pat. No. 3,507,891, this problem is solved by fractionated distillation of the reaction mixture obtained by alkoxycarbonylation, the cobalt used as the catalyst being obtained together with the distillation sump product.

With repeated or continued use, however, such a procedure results in an enrichment of high boiling point organic contaminations in the distillation sump product, as disclosed in West German Pat. No. 921,988 and European published application No. 00 08 024. Thereby the amount of residue continually grows and thus it must be fully reprocessed from time to time.

Reprocessing of the distillation sump product by boiling with a carboxylic acid or with water, as proposed in West German Pat. No. 921,988, entails difficulties, particularly in process engineering due to the tough and adhesive consistency of such residues. As the result of using carboxylic acids, the process suffers from corrosion problems and when boiling water is used, complete reprocessing of the water phase on ecological grounds is required.

The extraction of the distillation sump product using $CO_2$, $C_2$–$C_4$-paraffin, $C_2$–$C_4$ olefin or a halogen hydrocarbon above the critical temperature and the critical pressure of these compounds, as proposed in European published application No. 00 08 204, represents a problem without a simple solution in view of the required pressure exceeding 100 bars. Such a procedure also suffers from the dangers involved in using easily volatile and easily flammable compounds which include the lower olefins and paraffins. When the extraction is carried out with halogen hydrocarbons such as $CClF_3$, there is furthermore the danger of catalyst poisoning by the entrainment of halogen compounds into the alkoxycarbonylation reaction.

The requirement for reprocessing the distillation sump product can be circumvented by applying the method disclosed in U.S. Pat. No. 3,856,832 for catalyst recovery. In this method, a hydroesterification reaction is carried out in the presence of an excess of methanol as the esterification component and hydrocarbons are added to the completely reacted reaction mixture. Two phases are formed as a consequence. The lower phase contains at least 95% by weight of the cobalt used as catalyst and this lower phase can be fed directly back into the hydroesterification reaction.

The drawbacks of the method of U.S. Pat. No. 3,856,832 include its restriction to the production of methylesters and on the other hand the loss of the cobalt remaining in the upper phase which has a concentration up to 5% by weight.

The method of U.S. Pat. No. 4,041,057 achieves complete cobalt recovery by recovering the cobalt which in the method of U.S. Pat. No. 3,856,832 remains in the upper phase as a distillation sump product. The tarry residue so obtained is burned at temperatures of 1000° to 4000° F.

The cobalt oxide so formed is filtered out of the combustion gases, and the cobalt oxide is converted into cobalt carbonyl by reaction with carbon monoxide and hydrogen. This cobalt carbonyl is then fed back into the hydroesterification reaction.

While a complete recovery is possible in the combination of the methods of U.S. Pat. Nos. 3,856,832 and 4,041,057, the efficiency and profitability of such an overall process, however, remains considerably reduced by the use of substantial amounts of hydrocarbons which substantially load the distillation reprocessing and by a costly, multistage recovery of the residual cobalt contained in the upper phase.

SUMMARY OF THE INVENTION

Having in mind the limitations of the prior art, it is an object of the present invention to develop a generally applicable process which can be carried out commercially in simple and economical manner for the recovery of cobalt catalysts used in alkoxycarbonylation without loss.

According to the present invention, the alkoxycarbonylation process for the production of fatty acid esters by reacting olefins, alkanols and carbon monoxide in the presence of a cobalt catalyst and a promoter consisting of pyridine, non-orthosubstituted alkylpyridines, or a mixture thereof is improved upon by treating the alkoxycarbonylation reaction output with a gas containing oxygen in a non-damaging manner in two distillation stages.

The first distillation stage is operated at a higher pressure than the second to produce a distillate of cobalt compound and a concentrate accumulating as the sump product of the second distillation stage. This sump product contains all of the cobalt used as catalyst and the cobalt concentrate is incorporated into pyridine, a non-orthosubstituted alkylpyridine or a mixture thereof to form a suspension. The suspension is then treated by a mixture of carbon monoxide and hydrogen at a temperature of 100° to 250° C. and a pressure of at least 50 bars, and this treatment product is fed back into the fatty acid ester synthesis.

DESCRIPTION OF THE PREFERRED EMBODIMENTS

The new and unexpected results of the present invention are contrasted with the teachings of West German Pat. No. 19 63 804 and European published application No. 00 08 024. It could not have been expected that the distillation reprocessing of the present invention could avoid an enrichment of high boiling-point substances in the cobalt distillation sump products and that reprocessing these products to remove high boiling point substances could be dispensed with.

The process of the present invention can be applied in principle to all alkoxycarbonylation methods for the production of fatty acid esters wherein a catalyst consisting of a cobalt compound and pyridine, a non-orthosubstituted alkylpyridine or a mixture thereof is used. Typical methods are disclosed in U.S. Pat. No. 3,507,891 and U.S. patent application Ser. No. 125,482. The selection of the olefins used is the least critical of all process steps, that is, both straight chain or branched alpha-olefins and olefins with internal double bonds can be used. However, olefins with more than one double bond and such with substitutents, for instance groups of aryl, cyano, carboxymethyl and hydroxyl are also suitable.

As a rule, olefins having 2 to 40, preferably 6 to 20 C atoms are used, which are prepared by methods of the state of the art. For instance, alpha-olefins are obtained by oligomerizing ethylene by the Ziegler process as disclosed in German Pat. No. 878,560 and U.S. Pat. No. 3,310,600. The olefins are also prepared by wax-cracking, and olefins with internal double bonds are obtained by dehydrogenation or chlorination and ensuing dechlorination of paraffins as disclosed in British Pat. No. 1,037,868.

As regards the method of British Pat. No. 1,037,868, blends, that is, mixtures or paraffins of various C numbers are used as a rule, whereby the olefins so obtained lack a uniform C number.

Moreover, all conceivable isomeric forms are present naturally in these olefin mixtures. Besides the pure and possibly substituted olefins, those with paraffin contents up to 85% by weight are also useful. The paraffin content is caused by the fact that complete conversions are not achieved in the manufacture of the olefins, and the unconverted paraffins are not separated, or are only partly separated.

Besides the olefin used, the kind of alkanol that is reacted with the olefin and the carbon monoxide also is not critical for the process of the present invention. As a rule alkanols having 1 to 10 and preferably 1 to 4 C atoms are used. Typical representatives from the group of primary alcohols include, but are not limited to, methanol, ethanol, propanol-(1) and butanol-(1).

Furthermore, it does not matter which cobalt compound is used in the alkoxycarbonylation. Carbonyls of cobalt, for instance dicobaltoctacarbonyl, are just as suitable as carboxylic acid, cobalt salts such as cobalt acetate, cobalt naphthenate and cobalt-2-ethylhexanoate, and salts of cobalt with inorganic acids such as cobalt nitrate and cobalt sulfate. Preferably those carboxylic acid cobalt salts are used having anions corresponding to the acid group of the fatty acid esters formed in the alkoxycarbonylation.

Pyridine and all non-orthosubstituted alkylpyridines such as 3-picoline and 4-picoline, 3,4-lutidine and 3,5-lutidine and 3-ethylpyridine and 4-ethylpyridine or mixtures of these substances are suitable as promoters.

Lastly the conditions of reactions of alkoxycarbonylation are not significant to the process of the present invention. As a rule, alkoxycarbonylating processes are carried out at temperatures of 80° to 300° and preferably 150° to 220° C., and at carbon monoxide pressures from 10 to 800, preferably 100 to 300 bars.

What is process-critical for the present process is the oxidizing treatment of the reaction mixture prior to the recovery of the cobalt by using oxygen or a gas containing oxygen, preferably air, at temperatures from 20° to 150°, preferably 40° to 120° C. This treatment, which is already disclosed in U.S. Pat. No. 3,507,891, Column 4, lines 21-43, and U.S. patent application Ser. No. 125,482 is carried out until there is destruction of the volatile cobalt compounds.

In a preferred embodiment of application Ser. No. 125,482, the reaction mixture is treated at a temperature between about 20° and 100° C., preferably between 40° and 60° C. with an oxygenated gas, preferably air, until the cobalt compounds which result in the separation of metallic cobalt during the processing by distillation are destroyed by oxidation. This embodiment can be carried out for instance in a trickling column by circulating the oxygenated gas in counterflow to the reaction discharge. The destruction by oxidation is easily recognized in the change in color (from brown-orange to brown-violet).

Contrary to the statements made in the state of the art, it is found now that the steps of the present invention achieve such an extensive separation of all non-converted input materials and of all reaction products from the cobalt used as catalyst that no dilution of the cobalt being fed back can be observed. This is due to high boiling substances which are formed as by-products and which are enriched even at an arbitrarily repeated feedback of the same catalyst batch.

The reaction output which contains, as the essential ingredients, unconverted alkanol and olefin, fatty acid esters, the promoter and also cobalt compounds as catalysts is separated in two stages into a cobalt-free distillate and a concentrate containing all of the cobalt. The procedure is such that first the ingredients having lower boiling points are separated in a first stage. Among the lower boiling-point ingredients of the reaction mixture are, in general, compounds that can be easily evaporated at normal pressure, for instance the lower alkanols having 1 to 5 C atoms, olefins with up to 8 C atoms and pyridine.

The higher boiling-point ingredients of the reaction mixture together with the minor portions of the high boiling-point by-products formed during the process are separated as the distillate in a second distillation stage. The distillate of the second stage as a rule contains as its essential components: unconverted alkanol having more than 5 C atoms and olefins with more than 8 C atoms, the ester formed as a reaction product and the pyridine derivative used as a promoter. The kind of the separation of the reaction output into two distillate blends as a rule is determined by the particular composition of the reaction output. For a corresponding composition of the reaction mixture, other process modes obviously also are possible, which provide the distillate fractions or another composition than that stated above.

A problem which frequently must be overcome by alkoxycarbonylation is the production of methylesters in the surfactant range 11 to 20 C atoms in the fatty acid base of the esters by using pyridine or gamma- or beta-picoline as promoter. The separation problem arising in this case can be solved for instance in that methanol is separated in the first distillation stage, and in the second stage, essentially the promoter, unconverted olefin and the fatty acid methylester formed as reaction product, all as distillates.

The separation operations of the process of the present invention as a rule are carried out in two combined evaporators. Where the boiling points of the low boiling-point components of the reaction mixture being separated permit, the first distillation stage preferably is operated at normal pressure in a thin film evaporator or another evaporator, with a short dwell time of the product to be evaporated. The use of falling film evaporators was found especially advantageous for the solution of the separation problem which is to be carried out in the first stage, as in this manner apparatus incrustations are avoided wholly or extensively. The second distillation stage is operated at a pressure less than that of the first stage so as not to damage the product. Trouble-free permanent operation of this second stage is ensured especially when thin film evaporators are used as the distillation equipment. The pressure difference in the two distillation stages is not critical in principle and as a rule is so adjusted that the distillates of the two stages can be completely condensed using simple engineering means. However, examples of the pressure range of the first distillation stage can range from 0.1 to 1.5 bar. The second distillation stage pressure range is suitably 0.1 bar to 500 mbar, and the pressure difference between the first and second stages is 1.49 to 0.01 bar.

Independently of the selection of the separation conditions of the second distillation stage, the cobalt catalyst always is obtained as a sump product of the second distillation stage. Due to the steady removal of high boiling-point components in the operational conditions of the present invention, it is possible to keep the cobalt concentration of this sump product constant or nearly constant without incurring cobalt losses and even for an arbitrarily often repeated process.

For reasons of ease of handling, the distillation residue is not concentrated to cobalt contents exceeding 20% by weight. Cobalt contents less than 2% by weight are inappropriate as in such a procedure an unnecessarily large part of the reactor volume available for the alkoxycarbonylation would be blocked by the substances accompanying the cobalt.

Within this range, preferably within a range from 4 to 15% by weight, the cobalt concentration is adjusted in arbitrary manner by correspondingly selecting the separation conditions in the second distillation stage and, when desired, it is kept constant or nearly constant for an arbitrary number of catalyst circulations.

In an especially preferred embodiment of the process of the present invention, the separation conditions of the second distillation stage are selected so that a cobalt concentrate is obtained as the sump product which evinces a viscosity of $10^4$ to $5 \times 10^5$ mPa.s at 60° C. In this manner, the concentrate can reliably be moved by means of commercially available pumps.

Before the cobalt sump product is fed back into the alkoxycarbonylation reaction, it must be incorporated into the pyridine, the non-orthosubstituted alkylpyridine or a mixture thereof used as the promoter. The suspension so obtained is treated with a mixture of carbon monoxide and hydrogen at a temperature from 100° to 250° C. and a pressure of at least 50 bars.

The promoter recovered from the reaction discharge is preferably used to incorporate the cobalt sump product and any losses are compensated for by adding fresh promoter.

As a rule gas mixtures of 10 to 90, preferably 40 to 60% by volume of hydrogen are used to treat the suspension so obtained with a mixture of carbon monoxide and hydrogen.

The treating temperature is between 100° and 250° C., preferably between 120° and 200° C., and the total pressure is at least 50 bars. An upper critical limit of the total pressure is set not by the chemistry of the process, rather by the pressure-resistance of the available equipment. Preferably a pressure range of 100 to 400 bars is used.

The time of treatment is easily ascertained by trial and error. It depends most of all on the selected pressure and temperature conditions and as shown by experience should be at least 5 minutes.

Successful treatment on one hand is noted by the solid portions in the suspension used being dissolved, and on the other hand in that the catalytic solution so obtained is active again.

The treatment of the cobalt suspension with a mixture of carbon monoxide and hydrogen is carried out for instance in a pressure vessel, a cascade of pressure vessels or a tubular reactor.

The process of the present invention is explained in further detail in relation to the examples listed below.

EXAMPLE 1

(A) Alkoxycarbonylation

The mixture of input materials, which are present in the following molar ratios:

1 mole of n-dodecene (isomeric mixture with a dodecene-(1) proportion less than 1% by weight)
2 moles of methanol
0.3 moles of gamma-picoline
0.03 gram-atom of cobalt (in the form of a concentrate obtained by the reprocessing in the following step C and containing all of the input cobalt)

is continuously pumped into an agitating autoclave where it is made to react under the following conditions:

| reaction temperature | 185° C. |
|---|---|
| CO hot pressure | 180 bars |
| (CO contains 1% by volume of $H_2$) | |
| dwell time | 1.6 hours |

(B) Oxidation of the Reactor Output

The reaction output from the alkoxycarbonylation stage is continuously fed to the top and into a 1 m long trickling tower filled with $8 \times 8$ mm Raschig rings and is treated with air in counterflow under the following conditions:

| reaction temperature | 40° C. |
|---|---|
| pressure | 1 bar |
| liquid flow rate | 260 ml/cm$^2$ · h |

-continued

| | |
|---|---|
| air per liter of reaction output | 50 liter |

The exhaust gas leaving the trickling tower is rid of organic contents by condensation. These organic contents are fed back into the oxidized reaction output.

(C) Reprocessing of the Oxidized Reaction Discharge

The oxidized reaction discharge is continuously rid of unconverted methanol in a falling film evaporator under the following conditions:

| | |
|---|---|
| normal pressure | |
| temperature of the heating medium | 197° C. |
| discharged liquid temperature | 166° C. |
| by pumping-in non-evaporated liquid portions, a liquid load corresponding to 10 times the supplied amount is adjusted. | |

The sump product of the falling film evaporator is continuously rid of volatile components in a thin film evaporator and to an extent that the collecting sump product of the thin film evaporator (DSV) is a concentrate containing all of the cobalt, with a cobalt content of 8% by weight and a viscosity of $8.3 \times 10^4$ mPa.s (at 60° C.). The following conditions are observed in this separation operation:

| | |
|---|---|
| pressure at the transition point | 40 mbars |
| temperature of the heating medium | 252° C. |
| rotor rpm | 900 |

The distillates further obtained in distillation reprocessing in the first two distillation stages (falling film evaporator, thin film evaporator) provide a mixture of tridecanoic acid methylesters at a yield of 96% with respect to the converted olefin (55% conversion) and with a proportion of 79% in linear esters.

(D) Treating the Cobalt Concentrate with Carbon Monoxide and Hydrogen

The cobalt concentrate accumulating as the sump product of the thin film evaporator is mashed with gamma picoline recovered from the further distillation reprocessing and with the amount of fresh gamma-picoline required to replace the gamma-picoline losses and is treated in an agitated autoclave in continuous manner under the following conditions with a mixture of 50% by volume of CO and 50% by volume of $H_2$:

| | |
|---|---|
| reaction temperature | 170° C. |
| pressure | 200 bars |
| dwell time | 15 minutes |

After expansion to 4 bars, the output from this stage, fresh methanol and methanol obtained from the further distillation reprocessing and fresh olefin are continuously fed at the given molar ratios into the alkoxycarbonylation stage and again are reacted under the conditions stated in A.

Upon 100 circulations of the catalyst under the conditions described in A, B, C and D regarding reaction or reprocessing, the following results, listed in Table 1, were obtained:

TABLE 1

| Number of catalyst circulations | [%] Olefin conversion | [%] Ester Selectivity | [%] n-portion | Co content of DSV sump product [%] | Viscosity of DSV sump product [mPa · s] | Weight of DSV sump product: weights of all input materials except CO |
|---|---|---|---|---|---|---|
| 1 | 55 | 96 | 79 | 8.0 | $8.3 \cdot 10^4$ | 0.08 |
| 10 | 53 | 97 | 80 | 7.9 | $7.0 \cdot 10^4$ | 0.08 |
| 25 | 56 | 96 | 79 | 8.1 | $9.0 \cdot 10^4$ | 0.08 |
| 50 | 54 | 95 | 78 | 7.8 | $6.2 \cdot 10^4$ | 0.08 |
| 75 | 57 | 96 | 78 | 8.0 | $8.7 \cdot 10^4$ | 0.08 |
| 100 | 55 | 96 | 80 | 8.1 | $9.5 \cdot 10^4$ | 0.08 |

DSV = Thin Film Evaporator

EXAMPLE 2

Example 1 is repeated except that the n-dodecene isomeric mixture (with the dodecene-(1) proportion less than 1% by weight) used as input contains 0.29 parts by weight of non-olefinic compounds referred to 1 part by weight of olefin. These compounds accumulating together with the non-converted olefin in the further distillation reprocessing per example 1C and consisting of by-products formed during the alkoxycarbonylation or of contaminations accumulating in the output olefin.

In the further distillation reprocessing per example 1 C of the reaction mixture obtained per example 1A and B and containing such a contaminated olefin, the proportion in non-olefinic contaminations is kept constant by removing part of the olefin fraction.

The results for 30 circulations of the catalyst are listed in Table 2 below.

TABLE 2

| Number of catalyst circulations | [%] Olefin conversion | [%] Ester Selectivity | [%] n-portion | Co content of DSV sump product [%] | Viscosity of DSV sump product [mPa · s] | Weight of DSV sump product: weights of all input materials except CO |
|---|---|---|---|---|---|---|
| 1 | 51 | 95 | 80 | 7.9 | $9.5 \cdot 10^4$ | 0.07 |
| 5 | 50 | 96 | 81 | 7.8 | $10.1 \cdot 10^4$ | 0.07 |
| 10 | 49 | 97 | 79 | 8.0 | $9.2 \cdot 10^4$ | 0.07 |
| 20 | 50 | 96 | 80 | 8.1 | $9.5 \cdot 10^4$ | 0.07 |
| 30 | 50 | 96 | 80 | 8.0 | $8.9 \cdot 10^4$ | 0.07 |

EXAMPLE 3

Example 1 is repeated except that in lieu of the n-dodecene isomeric mixture, octene-(1) is used and the following molar ratios are observed:

1 moles of octene-1
3 moles of methanol
0.45 moles of gamma-picoline
0.015 gram-atom of cobalt and the alkoxycarbonylation reaction is carried out under the following conditions:

| reaction temperature | 165° C. |
|---|---|
| CO hot pressure | 270 bars |
| dwell time | 1.1 h |

Table 3 below lists the results for 30 circulations of the catalyst.

TABLE 3

| Number of catalyst circulations | [%] Olefin conversion | [%] Ester Selectivity | [%] n-portion | Co content of DSV sump product [%] | Viscosity of DSV sump product [mPa·s] | Weight of DSV sump product: weights of all input materials except CO |
|---|---|---|---|---|---|---|
| 1  | 61 | 96 | 83 | 10.7 | $1.4 \cdot 10^5$ | 0.03 |
| 5  | 62 | 97 | 84 | 10.5 | $1.3 \cdot 10^5$ | 0.03 |
| 10 | 60 | 97 | 84 | 10.8 | $1.6 \cdot 10^5$ | 0.03 |
| 20 | 59 | 98 | 85 | 10.6 | $1.5 \cdot 10^5$ | 0.03 |
| 30 | 61 | 97 | 84 | 10.8 | $1.7 \cdot 10^5$ | 0.03 |

We claim:

1. In a process for preparing an alkyl ester of a saturated aliphatic carboxylic acid by reacting olefin with alkanol and carbon monoxide in the presence of a catalyst consisting of a cobalt compound and a promoter selected from the group consisting of pyridine, non-ortho-substituted alkylpyridine, and mixtures thereof to form a reaction mixture, the improvement consisting essentially of recovering and reactivating said catalyst by:
   (a) treating said reaction mixture with a gas containing oxygen and forming an oxidized cobalt compound;
   (b) carrying out a first distillation in a first distillation stage at a given pressure to produce a first sump product containing said oxidized cobalt compound and a first distillate free of cobalt;
   (c) carrying out a second distillation of said first sump product in a second distillation stage at a pressure less than said given pressure to produce a second sump product containing substantially all of said oxidized cobalt compound as a cobalt concentrate free of promoter and a second distillate free of cobalt and containing said promoter, unconverted alkanol having more than 5 carbon atoms, olefins with more than 8 carbon atoms and said alkylester formed as a reaction product;
   (d) mixing all of said cobalt concentrate in said promoter to form a suspension;
   (e) treating said suspension with a mixture of carbon monoxide and hydrogen at a temperature of about 100° to 250° C. and at a pressure of at least 50 bars to form a treatment product; and
   (f) feeding back said treatment product to said reacting olefin with alkanol and carbon monoxide.

2. The process of claim 1 wherein said second sump product contains between about 2 to 20% by weight of cobalt.

3. The process of claim 2, wherein said second sump product has a viscosity of about $10^4$ to $5 \times 10^5$ mPa.s at 60° C.

4. The process of claim 3, wherein said first distillation is carried out in a falling film evaporator and said second distillation is carried out in a thin film evaporator.

5. The process of claim 3, wherein said pressure less than said given pressure is 0.01 to 1.49 bar less than said given pressure.

6. The process of claim 5 wherein said given pressure is 0.1 to 1.5 bar.

7. The process of claim 6 wherein said pressure less than said given pressure is 500 mbar to 0.1 bar.

8. The process of claim 5 wherein said second sump product contains between 4 and 15% by weight of cobalt.

* * * * *